United States Patent [19]

King

[11] 4,283,625
[45] Aug. 11, 1981

[54] X-RAY FLUORESCENCE ANALYSIS

[75] Inventor: Thomas C. King, Early, Tex.

[73] Assignee: Associated Metals & Minerals Corporation, New York, N.Y.

[21] Appl. No.: 57,451

[22] Filed: Jul. 13, 1979

[51] Int. Cl.³ ............................................. G01N 23/22
[52] U.S. Cl. ...................................... 250/272; 250/273
[58] Field of Search ............ 250/272, 273, 274, 277 R, 250/278, 279

[56] References Cited

U.S. PATENT DOCUMENTS

| | | | |
|---|---|---|---|
| 3,452,193 | 6/1969 | Petersen | 250/272 |
| 3,581,087 | 5/1971 | Brenkerhoff | 250/272 |
| 3,710,104 | 1/1973 | Pavlek | 250/272 |
| 4,016,419 | 4/1977 | Kotani | 250/273 |

*Primary Examiner*—Craig E. Church
*Attorney, Agent, or Firm*—Christie, Parker & Hale

[57] ABSTRACT

A sample is analyzed for the presence of an element by exposing it to radiation which causes the element to emit a characteristic radiation. Background radiation and the characteristic radiation are passed through a first filter which attenuates the characteristic radiation. The time required for a fixed amount of radiation to pass through the first filter is measured to establish a reference time. Radiation from the sample is then passed through a second filter which attenuates the characteristic radiation by an amount different from the first filter. The amount of radiation passing through the second filter is measured during a time interval substantially equal to the reference time. The difference between the two amounts of radiation indicates the amount of element in the sample and reduces errors due to samples of different composition and physical condition and due to variation of radiation intensity from the source.

24 Claims, 1 Drawing Figure

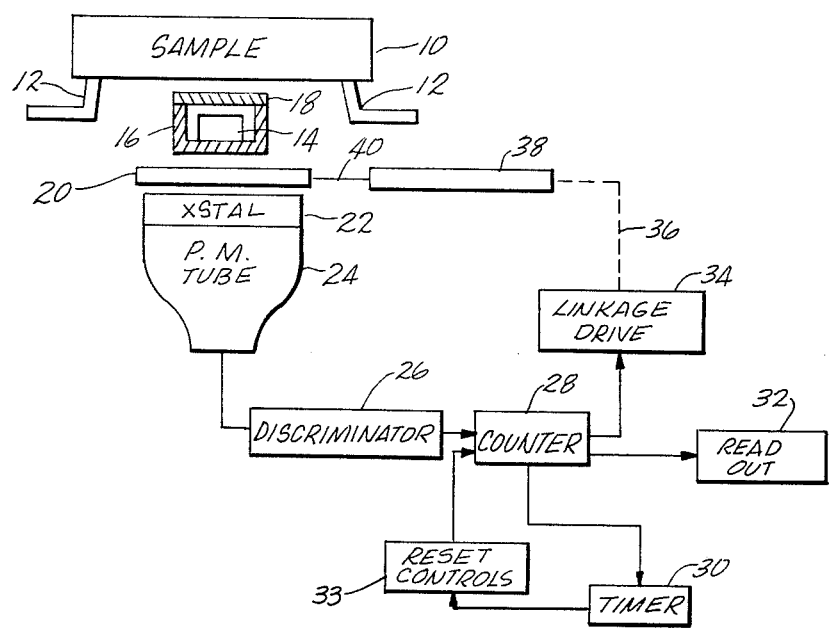

X-RAY FLUORESCENCE ANALYSIS

FIELD OF THE INVENTION

This invention relates to analysis of samples by x-ray fluorescence using a radiation source and absorption filters to isolate the desired x-rays and, more particularly, to the determination of the concentration of an element in the presence of other elements in a sample. The present invention reduces error due to variations in sample composition or condition, irregularities in sample distance from the measuring assembly, and variations in the irradiating source.

DESCRIPTION OF THE PRIOR ART

Various types of x-ray fluorescence analyzers have been used to determine the presence of an element in materials such as alloys, ores, paints, solutions, compounds, and the like. One such device is described in Ramsey Engineering Company Publication No. 710-715680, published July, 1978. That publication is an instruction manual for a portable analyzer which irradiates a sample with x-rays from a radioisotope source. That radiation causes x-ray fluorescence of the element to be detected. The irradiation from the source also creates unwanted background x-ray radiation. The radiation from the sample passes through a first filter to a scintillation crystal mounted on the face of a photomultiplier tube, which converts individual x-rays into electrical pulses with voltages approximately proportional to the energy of the individual x-ray striking the scintillation crystal. A single-channel analyzer amplifies the electrical pulses from the photomultiplier tube. A discriminator passes pulses within preset voltage limits, and a digital counter counts the pulses over a preset time interval. A multiple-channel analyzer is used if x-rays of different energy are to be separated by the discriminator and counted simultaneously.

The first filter (called the "upcount" filter) passes about half the x-ray radiation, including the desired x-rays. After the source irradiates the sample for a fixed, preset time, the total x-ray count (both the unwanted background and the wanted characteristic x-ray radiation from the element being analyzed) is recorded. The first filter is then replaced by a second filter (called the "down count" filter) which passes about half the background x-ray radiation, but substantially attenuates the desired x-rays from the element being analyzed. The radioisotope source then irradiates the sample for the same fixed, preset time, and the total x-ray count is recorded. The second count is subtracted from the first count, leaving a difference which is a function of the concentration of the desired element. Unfortunately, this determination is subject to error because of variations in sample composition and physical characteristics, the distance between the sample and the source, and variation in irradiation from the source. The fixed, preset time is increased occasionally in some cases by manual adjustment to the timer to compensate for source decay. However, this is left to the judgment of the operator and introduces an error subject to that judgment.

The errors suffered by the prior art apparatus and procedures have caused rejection of the method in many applications where it should theoretically provide significant advantages, such as improved time, accuracy, and cost, over competing methods. Even a small reduction in these errors in analysis would provide a significant commercial benefit.

This invention overcomes many of the shortcomings of the prior art by providing a system which automatically eliminates, or greatly reduces, the error due to variation in:
(1) sample composition;
(2) sample physical characteristics (surface area, density, etc.), and
(3) radiation from the source.

SUMMARY OF THE INVENTION

In terms of apparatus, this invention includes means for holding a sample which contains an element that fluoresces characteristic radiation when exposed to a source of radiation. The sample scatters and may fluoresce unwanted background radiation. Means are provided for irradiating the sample with a radiation of sufficient energy to cause the element to fluoresce the characteristic radiation.

The apparatus also includes a first filter which substantially attenuates the characteristic radiation, and a second filter which attenuates the characteristic radiation less than the first filter. Means are provided for sensing the radiation from the sample and for measuring the time required for the radiation sensing means to sense a fixed amount of radiation passing from the sample through one of the filters to the radiation sensing means to establish a reference time. Means are also provided for sensing the amount of radiation passing from the sample through the other filter to the sensing means during a time interval substantially equal to the reference time. Means are also provided for determining the difference between the two amounts of radiation passing through the two filters to indicate the amount of the element in the sample.

Preferably, the first filter attenuates most of the characteristic x-ray produced by fluorescence from the element, and the reference time is determined with the first filter disposed between the sample and the radiation sensing means. The energy of the radiation source is between 5 KeV and 140 KeV, and preferably has an energy between about 1.8 and 1.1 times that of the characteristic x-ray fluoresced by the element under analysis. In one form of the invention, a primary radioactive source bombards a secondary source to produce a source of radiation in the preferred energy range. Each filter absorbs about one-half the background radiation. Means are also provided for moving one of the filters to replace the other after the fixed amount of radiation has been measured to establish the reference time. When the radiation source is a radioisotope, means are preferably provided for shielding the sensing means from direct radiation from the source.

Preferably, the first filter attenuates the characteristic fluorescence from the element substantially more than it does the background radiation from the rest of the sample.

The preferred form of the apparatus also includes means for converting x-rays from the sample to electrical pulses proportional to the energy of the x-ray received from the sample, and discriminator means detect only those pulses within a fixed voltage range. The preferred apparatus also includes a digital counter which can count and display or record the number of pulses received from the discriminator. That counter also starts a timer when counting starts. When the count reaches a preset number, the counter stops the timer and automatically substitutes one filter for the other. Preferably, the timer stores the time interval required to count the fixed amount of radiation as the reference time, which is used to start and stop counter when the other filter is positioned between the source and the sensing means. In one form of the invention a digital counter is used to count negative when one of the filters is in operating position to a fixed negative number. The reference time is determined, and the counter then counts positive when the other filter is in operative position for a time interval equal to the reference time, so that the difference in counts through the two x-ray filters may be determined directly.

In terms of method, the invention reduces the effects of sample composition, physical condition, and variation of radiation intensity from a source used to analyze a sample for the presence of an element which fluoresces characteristic radiation when exposed to a source of radiation. The radiation from the sample passes through a first filter, which attenuates the characteristic radiation. The time required for a fixed amount of radiation to pass through the first filter is measured to establish a reference time. Thereafter, radiation from the sample is passed through a second filter, which attenuates the characteristic radiation by an amount different from the first filter. The amount of radiation passing through the second filter is measured during a time interval substantially equal to the reference time, and the difference between the two amounts of radiation is used as an indication of the amount of the element in the sample.

In the preferred method, a first filter attenuates the characteristic radiation from the element more than the second filter. The first filter also attenuates the characteristic radiation more than the background radiation from the sample. The second filter attenuates the background radiation about the same as the first filter. Preferably, each filter passes about one-half the total background radiation. In the preferred method, the first filter attenuates most of the characteristic fluorescent radiation from the element being determined. The energy of the radiation from the source is between about 5 and about 140 KeV and preferably is between about 1.8 and about 1.1 times that of the characteristic radiation. In one form of the invention, a primary source is used to radiate a secondary source to produce source radiation in the preferred range. The radiation passing the filters is converted to electrical pulses which are counted. The electrical pulses are proportional to the energy of the radiation creating them, and discriminating means are used to measure only those pulses within a selected energy range.

BRIEF DESCRIPTION OF THE DRAWING

The accompanying drawing shows in block diagram form the preferred embodiment of this invention.

DESCRIPTION OF PREFERRED EMBODIMENT

Referring to the drawing, a sample 10 is held on suitable supports 12 in the vicinity of a radiation source 14 disposed in a radiation shield 16, which has a removable cover 18. A first filter 20 is disposed between the sample and a scintillation crystal 22 mounted on the face of a photomultiplier tube 24, the output of which is connected to a pulse height discriminator 26, which is connected to a pulse counter 28, which may be of the digital type. The output of the counter controls a timer 30 and also is recorded in a readout device 32. The timer actuates reset controls 33, which govern the operation of the counter as described below.

The output of the counter is also connected to a linkage drive 34, connected through a linkage 36 to a second filter 38, which is connected by a link 40 to the first filter.

In operation, the apparatus shown in the drawing is supplied electrical power from a conventional source (not shown) and allowed to stabilize. The timer and digital radiation counter are set to zero.

The sample is placed on the supports, and the first filter is located as shown in the drawing. The first filter is designed to attenuate the characteristic fluorescent x-rays from the element for which analysis is to be made substantially more than it attenuates other x-rays (background radiation), such as those generated by fluorescence from other materials in the sample, or by back-scattering. Preferably, the first filter attenuates about one-half of the background x-ray radiation. The second filter also has the ability to attenuate about one-half the background x-ray radiation, but attenuates the characteristic fluorescent x-ray from the element in the sample substantially less than does the first filter, which preferably attenuates most of the characteristic fluorescent x-ray radiation from the element in the sample. The sample contains an element, say, tin which fluoresces a K alpha one 25.27 KeV x-ray when irradiated with x-ray radiation of higher energy, as is well known to those skilled in the art.

The cover 18 is removed from the shield 16, and the source 14, which may be a radioisotope, such as Americium 241, irradiates the sample, causing fluorescent and back-scattered x-rays to pass through the first filter and strike the scintillation crystal 22. The fluoresced and back-scattered x-rays are distinct from and lower in energy than those from the source. The x-ray radiation from the sample includes the characteristic fluorescent radiation of the element being analyzed, the characteristic radiation from other elements in the sample, and back-scattered radiation. The first filter is primarily made of an element whose K X-radiation absorption edge is just below or slightly lower in radiation energy than that of the desired characteristic x-ray fluorescence being emitted by the element under analysis in the sample. About half of the x-ray fluorescence and back-scattered radiation from the sample passes through the first filter, but the characteristic x-ray fluorescence from the element under analysis is greatly attenuated, perhaps as much as 98%. The filtered radiation enters the scintillation crystal, where the x-rays are converted into photon bursts proportional to the energy of the x-rays. The photon bursts are detected and converted into amplified electrical pulses by the photomultiplier tube. The output from the photomultiplier tube passes through a discriminator to effect pulse height selection, so that only x-rays within a selected energy range are counted. These selected pulses, random in nature, are counted by the digital counter until a preset number is reached, say, 64,000. When this fixed or preset number is reached, the digital counter stops and turns off the timer, which began operating at the start of the run. Thus, simultaneously with the counter reaching the fixed amount of counted radiation, the time interval required to reach that count is timed by the timer to establish a reference or matrix time. When the counter reaches the fixed number, it also actuates the linkage drive 34, which shifts the filters shown in the drawing from right to left, so that the second filter 38 takes the place of the first filter. The second filter is primarily made of an element whose K X-radiation absorption edge is just above or of slightly greater energy than the X-ray fluorescence from the element being analyzed in the sample.

The sample is now radiated by the same source and in the same manner as was done previously. However, this time the desired or characteristic x-ray from the element is not attenuated by the second filter as much as by the first, so that about half of the desired radiation passes through the second filter along with about half of the rest of the x-ray back-scattering and x-ray fluorescence from the sample. This transmitted x-ray irradiation reaches the scintillation crystal and is counted as previously described. However, the counter is automatically turned off by the timer after an interval has passed equal to the reference time previously established by the fixed amount of radiation passing through the first filter. At the end of that time interval, the timer and digital counter are reset, and the results displayed.

With the two filters properly balanced as described above, the net count, or the difference between the second radiation count and the first radiation count, is a function of the actual percentage of the element undergoing analysis in the sample, and is substantially free of those errors which are the principal shortcomings of the prior art, namely, those errors due to variations in sample composition, physical sample characteristics, and radiation from the source. Thus, this invention uses a different reference time interval with every sample. That interval is determined by the fixed radiation count through the first filter, and is used as the counting time for the radiation which passes through the second filter. This reference time is a measure of the matrix characteristics of the sample and can be recorded and used to generate information of value, such as the approximate iron content of the sample.

If desired, this reference time can be established by passing a fixed amount of radiation through the second filter, i.e., reversing the order in which the filters are used from that described above. However, I have found that better results are usually achieved by using the first filter to establish the reference time.

The accuracy of the analysis in accordance with this invention is further improved by irradiating the element to be determined with radiation which has an energy between about 1.8 and about 1.2 times the energy of the characteristic x-ray radiation fluoresced by the element being analyzed. When there is no suitable radioactive isotope to provide a source of radiation of the desired energy range, one can sometimes be created by bombarding a secondary source with irradiation from a primary source. For example, Americium 241 is a good radioactive isotope to use as a primary source because it has a relative long half-life of 458 years. However, the energy of its prominent x-ray radiation is about 59.5 KeV. Since this is over twice the characteristic radiation fluoresced by tin under x-ray bombardment, there is a mismatch between the source and the element being analyzed. Accordingly, a large amount of unwanted fluorescent x-rays are generated from other elements in the sample, and there is also a substantial amount of unwanted back-scattering. To reduce further this potential source of error, this invention includes the use of a secondary source, such as barium, which fluoresces two x-rays having respective energies of about 31.8 and about 32.2 KeV. Thus, by mixing the Americium with barium, a substantial flux of x-rays having energies of 31.8 and 32.2 KeV are generated. This permits the sample to be irradiated with substantially less of the 59.5 KeV x-rays from the Americium, resulting in less back-scattering and interference from other elements present in the sample. Consequently, the accuracy of the determination of the amount of tin present in the sample is significantly improved.

Conveniently, the apparatus shown in FIG. 1 can be set to count backwards, or negatively, through the first ("down count") filter for the fixed, preset count to determine the reference or matrix time. Then the counter can be set to count forward, or positively, through the second ("up count") filter for the previously determined reference or matrix time. The resulting net count is then displayed directly as an indication of concentration of the element being analyzed, provided the filters are properly balanced as described above.

I claim:

1. Apparatus for reducing the effects of sample composition and physical condition, and variation of radiation intensity from a source used to analyze a sample for the presence of an element which fluoresces characteristic radiation when exposed to a source of radiation, the apparatus comprising:
   means for holding the sample;
   means for irradiating the sample with a radiation of sufficient energy to cause the element to fluoresce the characteristic radiation;
   a first filter which substantially attenuates the characteristic radiation;
   a second filter which attenuates the characteristic radiation less than the first filter;
   means for sensing radiation from the sample;
   means for measuring the time required for the radiation sensing means to sense a fixed amount of radiation from the sample when one of the filters is between the sample and radiation sensing means to establish a reference time;
   means for measuring the amount of radiation from the sample reaching the sensing means during a time interval substantially equal to the reference time when the other filter is disposed between the sample and the sensing means; and
   means for determining the difference between the two amounts of radiation reaching the sensing means through the two filters to indicate the amount of the element in the sample.

2. Apparatus according to claim 1 in which the first filter attenuates most of the characteristic x-ray.

3. Apparatus according to claim 1 in which the first filter is used to determine the reference time.

4. Apparatus according to claim 1 in which the radiation source emits x-rays in the energy range of about 5 to about 140 KeV.

5. Apparatus according to claim 1 in which each filter absorbs about one-half the radiation passing through it.

6. Apparatus according to claim 1 which includes means for automatically moving the second filter to replace the first filter after the fixed amount of radiation is measured.

7. Apparatus according to claim 1 in which the first filter attenuates the characteristic x-ray of the element being analyzed more than x-rays from the rest of the sample.

8. Apparatus according to claim 1 which includes means for shielding the sensing means from direct radiation from the source.

9. Apparatus according to claim 1 which includes means for converting x-rays reaching the sensing means into electrical pulses proportional to the energy of the x-rays.

10. Apparatus according to claim 9 which includes discriminator means for counting only those electrical pulses within a selected range of values.

11. Apparatus according to claim 1 which includes means responsive to the counter to change filters automatically when the fixed amount of radiation has been measured.

12. Apparatus according to claim 1 which includes a timer for measuring the amount of time required to sense the fixed amount of radiation.

13. Apparatus according to claim 1 or 12 in which the energy of the radiation from the source is between about 1.8 and about 1.3 times that of the characteristic radiation fluoresced by the element being analyzed.

14. A method for reducing the effects of sample composition, physical condition, and variation of radiation intensity from a source used to analyze a sample for the presence of an element which fluoresces characteristic radiation when exposed to a source of radiation, the method comprising the steps of:
   irradiating the sample with a source of radiation of sufficient energy to cause the element to fluoresce the characteristic radiation;
   passing radiation from the sample through a first filter which attenuates the characteristic radiation;
   measuring the time required for a fixed amount of radiation to pass through the first filter to establish a reference time;
   passing radiation from the sample through a second filter which attenuates the characteristic radiation by an amount different from the first filter;
   measuring the amount of radiation which passes through the second filter during a time interval substantially equal to the reference time; and
   determining the difference between the two amounts of radiation as an indication of the amount of the element in the sample.

15. A method according to claim 14 in which the radiation source emits x-rays having an energy between about 5 and about 140 KeV.

16. A method according to claim 14 in which the first filter attenuates the characteristic radiation substantially more than the second filter.

17. A method according to claim 14 or 16 in which the first filter attenuates the characteristic radiation more than other radiation emitted by the sample.

18. A method according to claim 17 in which the second filter attenuates the other radiation from the sample about the same as the first filter.

19. A method according to claim 14 in which both filters attenuate radiation from the sample other than the characteristic radiation about the same amount.

20. A method according to claim 19 in which both filters attenuate the said other radiation by about 50%.

21. A method according to claim 14 which includes the step of attenuating most of the characteristic radiation while determining the reference time.

22. A method according to claim 14 which includes the step of converting the radiation passing through the filters to electrical pulses, and counting the pulses to determine the radiation.

23. A method according to claim 22 which includes the step of converting the radiation passing the filters to electrical pulses proportional to the energy of the radiation, and counting only those electrical pulses within a fixed range of values.

24. A method according to claim 14 or 23 in which the energy from the source is between about 1.8 and 1.1 times the energy of the characteristic radiation fluoresced by the element being analyzed.

* * * * *